(12) United States Patent
Taylor et al.

(10) Patent No.: US 6,635,602 B1
(45) Date of Patent: Oct. 21, 2003

(54) PREPARATION PROCESS FOR MANUFACTURE AND PURIFICATION OF MIXTURES OF FLUORAN COMPOUNDS AND RECORDING MATERIAL COMPRISING SAID MIXTURES OF FLUORAN COMPOUNDS

(75) Inventors: James Philip Taylor, Macclesfield (GB); Michael Heneghan, Rheinfelden-Adelhausen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/763,736

(22) PCT Filed: Aug. 10, 1999

(86) PCT No.: PCT/EP99/05808

§ 371 (c)(1),
(2), (4) Date: Feb. 26, 2001

(87) PCT Pub. No.: WO00/12513

PCT Pub. Date: Mar. 9, 2000

(30) Foreign Application Priority Data

Aug. 29, 1998  (GB) ............................................. 9818836

(51) Int. Cl.$^7$ ............................ B41M 5/20; B41M 5/24
(52) U.S. Cl. ...................... 503/221; 106/31.22; 546/15; 549/224; 549/225; 549/226
(58) Field of Search .......................... 503/221; 549/224, 549/225, 226; 546/15; 106/31.22

(56) References Cited

U.S. PATENT DOCUMENTS

| 4,226,912 A | 10/1980 | Iwasaki et al. ............. 428/411 |
| 5,166,350 A | 11/1992 | Bedekovic et al. ........... 546/15 |

FOREIGN PATENT DOCUMENTS

| DE | 2316664 | 10/1974 |
| EP | 0095114 | 11/1983 |
| EP | 0098151 | 1/1984 |
| EP | 0122318 | 10/1984 |
| GB | 1336955 | 11/1973 |
| GB | 2051849 | 1/1981 |
| GB | 2199669 | 7/1988 |

Primary Examiner—Bruce H. Hess
(74) Attorney, Agent, or Firm—Kevin T. Mansfield

(57) ABSTRACT

A process for the manufacture of mixtures of fluoran compounds by the reaction of keto acids of formula (II) with a compound of formula (III) in the presence of a dehydrating condensation agent, wherein R1 and R2 independently represent hydrogen; an alkyl of 1–18 carbon, a secondary alkyl with respect to the carbon atom bonded to the nitrogen atom of 3–13 carbon atoms, a cycloalkyl of 4–8 carbon atoms or a phenyl, both of which may be substituted by at least one substituted selected from the group consisting of halogen atoms and alkyls having 1–4 carbon atoms, an aralkyl of 7–10 carbon atoms; or R1 and R2, together with the adjacent nitrogen atom from a heterocyclic ring; R3 is hydrogen, an alkyl of 1–4 carbon atoms, an alkoxy of 1–4 carbon atoms, a phenyl; a substituted phenyl or a halogen; R4 is an alkyl group of 1–18 carbon atoms, a carboxyalkyl of 1–18 carbon atoms, a carboxycycloalkyl of 4–8 carbon atoms, an alkylamino of 1–18 carbon atoms, a cycloalkylamino of 4–8 carbon atoms, a dialkylamino or dicycloalkylamino; an arylamino, a substituted arylamino; an aralkylamino of 7–10 carbon atoms; a diaralkylamino; R5 is an alkyl of 1–18 carbon atoms, a carboxy alkyl of 1–18 carbon atoms or a halogen and R6 is hydrogen or alkyl of 1–4 carbon atoms.

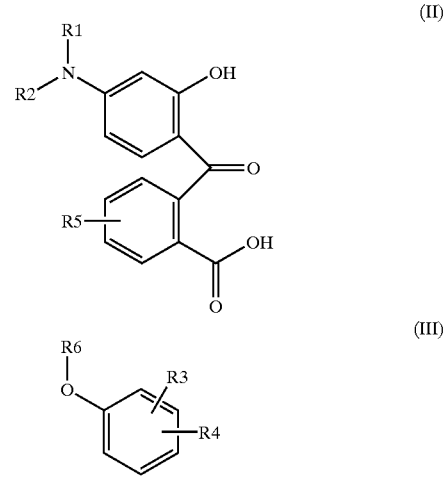

13 Claims, No Drawings

ND PURIFICATION OF
PREPARATION PROCESS FOR MANUFACTURE AND PURIFICATION OF MIXTURES OF FLUORAN COMPOUNDS AND RECORDING MATERIAL COMPRISING SAID MIXTURES OF FLUORAN COMPOUNDS

TECHNICAL FIELD

The present invention relates to mixtures of fluoran compounds which are useful as colour forming compounds in recording materials. More particularly, the invention relates to a process for the preparation of said mixtures of fluoran compounds and to the use of said mixtures of fluoran compounds as colour formers in recording materials such as heat sensitive and pressure sensitive recording materials.

DESCRIPTION OF THE PRIOR ART

Pressure sensitive recording, heat sensitive recording and electroheat sensitive recording have conventionally been used as systems for recording transferred information through the mediation of external energy, such as pressure, heat or electricity, by utilising a colour reaction between a colourless or pale coloured electron donative compound (colour forming compound) and an organic or inorganic electron acceptor (developer).

In such recording systems, mixtures of more than one colour former have been used as the colour forming compound. For example, U.S. Pat. No. 4,226,912 discloses a system wherein the chromogenic material is a physical mixture of two black fluoran colour formers in a heat sensitive recording system. At present, such mixtures of fluorans are prepared by physical mixing of the component fluoran colour formers. Where a mixture of more than one colour former is to be used then, an additional mixing step is necessary in the preparation of the final recording system. It is advantageous to mix thoroughly in order to generate a homogenous system. To achieve good mixing the intensity of mixing and the time of mixing can be altered. However, unless separate analysis of the mixture is carried out the relative composition of the dispersed system is unknown. In addition, where two or more colour formers are used the relative purity/impurity of each component may have an impact on the final characteristics of the recording material. As such, the formulators challenge is to develop a multi-colour former system in which the individual components are present at optimal purity levels in order to deliver desirable recording properties and yet which can be manufactured both simply and efficiently.

It has now been found that mixtures of specified fluoran colour forming compounds can be synthesised directly by the reaction of at least two derivatives of amino phenols, phthalic anhydrides, keto acids and/or diphenylamines with a phenol derivative. The advantages of the present process are that a separate mixing step in the preparation of the final recording system is obviated with the relevant savings in time and energy in the process and the relative impact of mixed impurities or impurity levels from differing colour former components is reduced.

OBJECT OF THE INVENTION

An object of the present invention is to provide an efficient process for the manufacture of mixtures of fluoran compounds that does not require separate manufacture of the individual component fluoran compounds, subsequent mixing and further treatment of the mixture. Thus the present invention provides a novel process for the manufacture of mixtures of fluoran compounds from appropriate mixtures of starting materials in a single process.

DETAILED DESCRIPTION OF THE INVENTION

The mixtures of fluorans prepared by the present invention may be amorphous mixtures, mixed crystals, monophase solid solutions, multiphase solid solutions, aggregates of different compounds each in pure crystal modification and mixtures thereof.

In the literature, the definitions by the various authors, such as, G. H. Van't Hoff, A. I. Kitaigorodsky and A. Whitacker for solid solutions and mixed crystals are often contradictory, (cf, e.g. 'Analytical Chemistry of Synthetic Dyes', Chapter 10/page 269. Editor K. Venkataraman, J. Wiley, New York, 1977). The term 'monophase solid solution' or 'multiphase solid solution' or mixed crystal', as defined herein, therefore, should be taken from the following definitions, which have been adapted to the current improved state of knowledge of such systems:

A monophase (or single-phase or guest-host) solid solution possesses a crystal lattice which is identical with the crystal lattice of one of its components. One component is embedded as the 'guest' in the crystal lattice of the other component, which acts as the 'host'. The X-ray diffraction pattern of such a monophase solid solution is substantially identical to that of one of the components, called the 'host'. Within certain limits, different proportions of the components produce almost identical results.

A multiphase solid solution possesses no precise, uniform crystal lattice. It differs from a physical mixture of its components in that the crystal lattice of at least one of its components is partially or completely altered. In comparison to a physical mixture of the components, which gives an X-ray diffraction diagram that is additive of the diagrams seen for the individual components. The signals in the X-ray diffraction diagram of a multiphase solid solution are broadened, shifted or altered in intensity. In general, different proportions of the components produce different results.

A mixed crystal (or solid compound type) solid solution possesses a precise composition and a uniform crystal lattice, which is different from the crystal lattices of all its components. If different proportions of the components lead, within certain limits, to the same result, then a solid solution is present in which the mixed crystal acts as a host.

As hereinbefore detailed, the novel mixtures of fluorans comprise a plurality of colour forming compounds. Suitable mixtures of fluoran colour forming materials which may be prepared according to the present invention may include at least one fluoran compound such as 3-dibutylamino-7-dibenzylaminofluoran, 3-diethylamino-6-methylfluoran, 3-dimethylamino-6-methyl-7-anilinofluoran, 3-diethylamino-6-methyl-7-anilinofluoran, 3-diethylamino-6-methyl-7-(2,4-dimethylanilino)fluoran, 3-diethylamino-methyl-7-chlorofluoran, 3-diethylamino-6-methyl-7-(3-trifluoromethylanilino)fluoran, 3-diethylamino-6-methyl-7-

(2-chloroanilino)fluoran, 3-diethylamino-6-methyl-7-(4-chloroanilino)fluoran, 3-diethylamino-6-methyl-7-(2-fluoroanilino)fluoran, 3-diethylamino-6-methyl-7-(4-n-octylanilino)fluoran, 3-diethylamino-7-(4-n-octylanilino)fluoran, 3-diethylamino-7-(n-octylamino)fluoran, 3-diethylamino-6-methyl-7-(dibenzylamino)fluoran, 3-diethylamino-7-(dibenzylamino)fluoran, 3-diethylamino-6-chloro-7-methylfluoran, 3-diethylamino-7-t-butylfluoran, 3-diethylamino-7-carboxyethylfluoran, 3-diethylamino-6-chloro-7-anilinofluoran, 3-diethylamino-6-methyl-7-(3-methylanilino)fluoran, 3-diethylamino4—methyl-7-(4-methylanilino)fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino)fluoran, 3-diethylamino-7-(2-chloroanilino)fluoran, 3-diethylamino-7-(2-fluoroanilino)fluoran, 3-diethylamino-benzo[a]fluoran, 3-diethylamino-benzo[c]fluoran, 3-dibutylamino-6-methyl fluoran, 3-dibutylamino-methyl-7-anilinofluoran, 3-dibutylamino-6-methyl-7-(2,4-dimethylanilino)fluoran, 3-dibutylamino-6-methyl-7-(2-chloroanilino)fluoran, 3-dibutylamino-6-methyl-7-(4-chloroanilino)fluoran, 3-dibutylamino-6-methyl-7-(2-fluoroanilino)fluoran, 3-dibutylamino-6-methyl-7-(3-trifluoromethylanilino)fluoran, 3-dibutylamino-6-ethoxyethyl-7-anilinofluoran, 3-dibutylamino-6-chloro-anilinofluoran, 3-dibutylamino-6-methyl-7-(4-methylanilino)fluoran, 3-dibutylamino-7-(2-chloroanilino)fluoran, 3-dibutylamino-7-(2-fluoroanilino)fluoran, 3-dipentylamino-6-methyl-7-anilinofluoran, 3-dipentylamino-6-methyl-7-(4-chloroanilino)fluoran, 3-dipentylamino-7-(3-trifluoromethylanilino)fluoran, 3-dipentylamino-6-chloro-7-anilinofluoran, 3-dipentylamino-7-(4-chloroanilino)fluoran, 3-pyrrolidino-6-methyl-7-anilinofluoran, 3-piperidino-6-methyl-7-anilinofluoran, 3-(N-methyl-N-propylamino)-methyl-7-anilinofluoran, 3-(N-methyl-N-cyclohexylamino)-6-methyl-7-anilinofluoran, 3-(N-ethyl-N-cyclohexylamino)-4-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino)-methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-methyl-7-anilinofluoran, 3-cyclohexylamino-6-chlorofluoran, 2-methyl-6-p-(p-dimethylaminophenyl)aminoanilinofluoran, 2-methoxy-4-p-(p-dimethylaminophenyl)aminoanilinofluoran, 2-chloro-3-methyl-6-p-(p-phenylaminophenyl)aminoanilinofluoran, 2-diethylamino-6-p-(p-dimethylaminophenyl)aminoanilinofluoran, 2-phenyl-6-methyl-6-p-(p-phenylaminophenyl)aminoanilinofluoran, 2-benzyl4-p-(p-phenylaminophenyl)aminoanilinofluoran, 3-methyl-6-p-(p-dimethylaminophenyl)aminoanilinofluoran, 3-diethylamino-6-p-(p-diethylaminophenyl)aminoanilinofluoran, 3-diethylamino-6-p-(p-dibutylaminophenyl)aminoanilinofluoran, 2,4-dimethyl—[(4-dimethylamino)anilino]fluoran, 3-[(4-dimethylaminophenyl)amino]-5,7-dimethylfluoran.

Highly preferred mixtures of fluoran colour formers according to the present invention are composed of at least two fluoran compounds of the general formula (I).

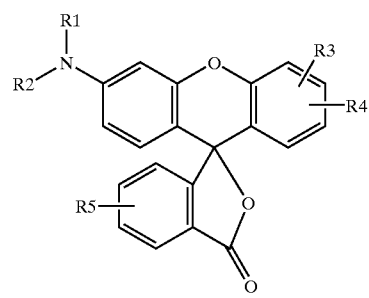

Formula I

Wherein R1 and R2 independently represent hydrogen; an alkyl of 1–18 carbon, a secondary alkyl with respect to the carbon atom bonded to the nitrogen atom of 3–13 carbon atoms; a cycloalkyl of 4–8 carbon atoms or a phenyl, both of which may be substituted by at least one substituent selected from the group consisting of halogen atoms and alkyls having 1–4 carbon atoms, an aralkyl of 7–10 carbon atoms. Alternatively, R1 and R2, together with the adjacent nitrogen atom may form a heterocyclic ring. R3 is hydrogen; an alkyl of 1–4 carbon atoms; an alkoxy of 1–4 carbon atoms; a phenyl; a substituted phenyl or a halogen. R4 is an alkyl group of 1–18 carbon atoms, a carboxyalkyl of 1–18 carbon atoms; a carboxycycloalkyl of 4–8 carbon atoms; a alkylamino of 1–18 carbon atoms; a cycloalkylamino of 4–8 carbon atoms; a dialkylamino or dicycloalkylamino as previously defined: an arylamino; a substituted arylamino; an aralkylamino of 7–10 carbon atoms; a diaralkylamino as previously defined. R5 is an alkyl of 1–18 carbon atoms; a carboxy alkyl of 1–18 carbon atoms or a halogen.

The ratio of the components being in the range 0.1–99% by mole.

Highly preferred are the following exemplary mixtures of fluorans comprising two components A and B in the stated ratios: 3-dibutylamino4-methyl-7-anilinofluoran (95%), 3-dibutylamino-7-dibenzylaminofluoran (5%); 3-dibutylamino6-methyl-7-anilinofluoran (90%), 3-diethylamino-6-methyl-7-anilinofluoran (10%); 3-dibutylamino-6-methyl-7-anilinofluoran (46%), 3-diethylamino-6-methyl-7-anilinofluoran (56%); 3-dibutylamino-6-methyl-7-anilinofluoran (52%), 3-diethylamino-6,3'(4')-dimethyl-7-anilinofluoran (48%); 3-diethylamino-6-methyl-7-anilinofluoran (10%), 3-N-(1-ethylpropyl)-N-propylamino-6-methyl-7-anilinofluoran (90%); 3-dibutylamino-6-methyl-7-m-tolylaminofluoran (10%), 3-dibutylamino-6-methyl-7-anilinofluoran (90%).

The mixtures of fluoran colour formers are prepared from mixtures of the appropriate starting materials. Such a methodology is novel and can be used to produce amorphous mixtures, monophase solid solutions, multiphase solid solutions and mixed crystals. The technique can be used to produce mixtures of two or more fluorans. Preferably, mixtures of two fluorans are produced by replacing a single starting material with two analogous materials to the same or similar total molar concentration in the reaction. In the case of fluorans, these starting materials are derivatives of amino phenols, phthalic anhydrides, keto acids and diphenylamines. The mixtures of starting materials may themselves be physical mixtures, monophase solid solutions, multiphase solid solutions, mixed crystals, aggregates of the different compounds each in pure crystal form or mixtures thereof. By utilising mixtures of more than one starting material it is possible to produce mixtures of more than two fluorans.

For instance, the controlled reaction of an appropriate mixture of keto acids of formula (II) and compound(s) of formula (Ill) will produce a mixture of fluoran colour formers. R1–R5 have the meanings given previously and R6 is a hydrogen or an alkyl of 1–4 C atoms.

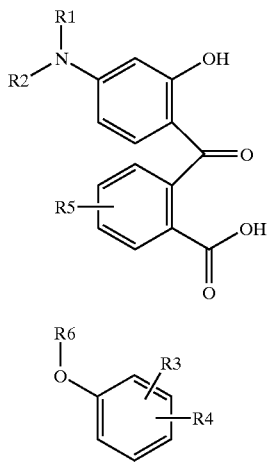

Formula II

Formula III

A mixture of n different fluorans, where n>1 may be manufactured by the reaction of x different keto acids of formula (II) and y different compounds of formula (III) where one or both of x and y are >1.

For instance, a mixture consisting of two compounds of general formula (I) may be prepared by reaction of;
 i. Two different keto acids of general formula (II) with a single compound of general formula (III).
 ii. Two different compounds of general formula (III) with a single keto acid of formula (II).

Compounds of general formula II are exemplified by, but not limited to; 2-hydroxy-4-N,N-di-methyl amino-2'-carboxybenzophenone, 2-hydroxy-4-N,N-di-ethyl amino-2'-carboxybenzophenone, 2-hydroxy-4-N,N-di-n-propyl amino-2'-carboxybenzophenone, 2-hydroxy4-N,N-di-n-butyl amino-2'-carboxybenzophenone, 2-hydroxy-4-N,N-di-n-pentyl amino2'-carboxybenzophenone, 2-hydroxy-4-N,N-di-n-hexyl amino-2'-carboxybenzophenone, 2-hydroxy-4-N,N-diisopropyl amino-2'-carboxybenzophenone, 2-hydroxy-4-N,N-diisobutyl amino-2'-carboxybenzophenone, 2-hydroxy-4-N,N-diisobutyl amino2'-carboxybenzophenone, 2-hydroxy-4-N,N-diisoamyl amino-2'-carboxybenzophenone, 2-hydroxy-4-N-methyl-N-cyclohexyl amino-2'-carboxybenzophenone, 2-hydroxy-4-N-methyl-N-phenyl amino-2'-carboxybenzophenone, 2-hydroxy-4-N-methyl-N-(2-methylphenyl)amino-2'-carboxybenzophenone, 2-hydroxy-4-N-methyl-N-(3-methylphenyl)amino-2'-carboxybenzophenone, 2-hydroxy-4-N-methyl-N-(4-methylphenyl)amino-2'-carboxybenzophenone, 2-hydroxy-4-N-methyl-N-propyl amino-2'-carboxybenzophenone, 2-hydroxy-4-N-methyl-N-isopropyl amino-2'-carboxybenzophenone, 2-hydroxy-4-N-methyl-N-butyl amino-2'-carboxybenzophenone, 2-hydroxy-4-N-methyl-N-isobutyl amino-2'-carboxybenzophenone, 2-hydroxy-4-N-methyl-N-secbutyl amino-2'-carboxybenzophenone, 2-hydroxy-4-N-methyl-N-pentyl amino-2'-carboxybenzophenone, 2-hydroxy-4-N-methyl-N-1-methylbutyl amino-2'-carboxybenzophenone, 2-hydroxy-4-N-methyl-N-isoamyl amino-2'-carboxybenzophenone, 2-hydroxy-4-N-methyl-N-1-methylpentyl amino-2'-carboxybenzophenone, 2-hydroxy-4-N-methyl-N-hexyl amino-2'-carboxybenzophenone, 2-hydroxy-4-N-methyl-N-tetrahydrofurylmethyl amino-2'-carboxybenzophenone, 2-hydroxy-4-N-methyl-N-ethoxypropyl amino-2'-carboxybenzophenone, 2-hydroxy-4-N-methyl-N-cyclohexylmethyl amino-2'-carboxybenzophenone, 2-hydroxy-4-N-methyl-N-phenethyl amino-2'-carboxybenzophenone, 2-hydroxy4N-ethyl-N-cyclohexyl amino-2'-carboxybenzophenone, 2-hydroxy-4-N-ethyl-N-phenyl amino-2'-carboxybenzophenone, 2-hydroxy-4-N-ethyl-N-(2-methylphenyl)amino-2'-carboxybenzophenone, 2-hydroxy-4-N-ethyl-N-(3-methylphenyl)amino-2'-carboxybenzophenone, 2-hydroxy-4-N-ethyl-N-(4-methylphenyl)amino-2'-carboxybenzophenone, 2-hydroxy-4-N-ethyl-N-propyl amino-2'-carboxybenzophenone, 2-hydroxy-4-N-ethyl-N-isopropyl amino-2'-carboxybenzophenone, 2-hydroxy4-N-ethyl-N-butyl amino-2'-carboxybenzophenone, 2-hydroxy-4-N-ethyl-N-isobutyl amino-2'-carboxybenzophenone, 2-hydroxy4-N-ethyl-N-secbutyl amino-2'-carboxybenzophenone, 2-hydroxy-4-N-ethyl-N-pentyl amino-2'-carboxybenzophenone, 2-hydroxy4-N-ethyl-N-1-methylbutyl amino-2'-carboxybenzophenone, 2-hydroxy-4-N-ethyl-N-isoamyl amino-2'-carboxybenzophenone, 2-hydroxy-4-N-ethyl-N-1-methylpentyl amino-2'-carboxybenzophenone, 2-hydroxy-4-N-ethyl-N-hexyl amino-2'-carboxybenzophenone, 2-hydroxy-4-N-ethyl-N-tetrahydrofurylmethyl amino-2'-carboxybenzophenone, 2-hydroxy4-N-ethyl-N-ethoxypropyl amino-2'-carboxybenzophenone, 2-hydroxy-4-N-ethyl-N-cyclohexylmethyl amino-2'-carboxybenzophenone, 2-hydroxy-4-N-ethyl-N-phenethyl amino-2'-carboxybenzophenone, 2-hydroxy-4-N-propyl-N-cyclohexyl amino-2'-carboxybenzophenone, 2-hydroxy-4-N-propyl-N-phenyl amino-2'-carboxybenzophenone, 2-hydroxy-4-N-propyl-N-(2-methylphenyl)amino-2'-carboxybenzophenone, 2-hydroxy-4-N-propyl-N-(3-methylphenyl)amino-2'-carboxybenzophenone, 2-hydroxy-4-N-propyl-N-(4-methylphenyl)amino-2'-carboxybenzophenone, 2-hydroxy-4-N-propyl-N-isopropyl amino-2'-carboxybenzophenone, 2-hydroxy-4-N-propyl-N-butyl amino-2'-carboxybenzophenone, 2-hydroxy-4-N-propyl-N-isobutyl amino-2'-carboxybenzophenone, 2-hydroxy-4-N-propyl-N-secbutyl amino-2'-carboxybenzophenone, 2-hydroxy-4-N-propyl-N-pentyl amino-2'-carboxybenzophenone, 2-hydroxy-4-N-propyl-N-1-methylbutyl amino-2'-carboxybenzophenone, 2-hydroxy-4-N-propyl-N-isoamyl amino-2'-carboxybenzophenone, 2-hydroxy4-N-propyl-N-1-methylpentyl amino-2'-carboxybenzophenone, 2-hydroxy-4-N-propyl-N-hexyl amino-2'-carboxybenzophenone, 2-hydroxy-4-N-propyl-N-tetrahydrofurylmethyl amino-2'-carboxybenzophenone, 2-hydroxy-4-N-propyl-N-ethoxypropyl amino-2'-carboxybenzophenone, 2-hydroxy-4-N-propyl-N-cyclohexylmethyl amino-2'-carboxybenzophenone, 2-hydroxy-4-N-propyl-N-phenethyl amino-2'-carboxybenzophenone, 2-hydroxy-4-N-butyl-N-cyclohexyl amino-2'-carboxybenzophenone, 2-hydroxy-4-N-butyl-N-phenyl amino-2'-carboxybenzophenone, 2-hydroxy-4-N-butyl-N-(2-methylphenyl)amino-2'-carboxybenzophenone, 2-hydroxy-4-N-butyl-N-(3-methylphenyl)amino-2'-carboxybenzophenone, 2-hydroxy-4-N-butyl-N-(4-methylphenyl)amino-2'-carboxybenzophenone, 2-hydroxy-4-N-butyl-N-propyl amino-2'-carboxybenzophenone, 2-hydroxy-4-N-butyl-N-isopropyl amino-2'- carboxybenzophenone, 2-hydroxy-4-N-butyl-N-isobutyl amino-2'-carboxybenzophenone, 2-hydroxy-4-N-butyl-N-secbutyl amino-2'-carboxybenzophenone, 2-hydroxy-4-N-butyl-N-pentyl amino-2'-carboxybenzophenone, 2-hydroxy-4-N-butyl-N-1-methylbutyl amino-2'-carboxybenzophenone, 2-hydroxy-4-N-butyl-N-isoamyl amino-2'-carboxybenzophenone, 2-hydroxy-4-N-butyl-N-1-methylpentyl amino-2'-carboxybenzophenone, 2-hydroxy-4-N-butyl-N-hexyl amino-2'-carboxybenzophenone, 2-hydroxy-4-N-butyl-N-tetrahydrofurylmethyl amino-2'-carboxybenzophenone, 2-hydroxy-4-N-butyl-N-ethoxypropyl amino-2'-carboxybenzophenone, 2-hydroxy-4-N-butyl-N-cyclohexylmethyl amino-2'-carboxybenzophenone, 2-hydroxy-4-N-butyl-N-phenethyl amino-2'-carboxybenzophenone, 2-hydroxy-4-N-phenyl amino-2'-carboxybenzophenone, 2-hydroxy-N-(2-methylphenyl)amino-2'-carboxybenzophenone, 2-hydroxy-4-N-(3-methylphenyl)amino-2'-carboxybenzophenone, 2-hydroxy-4-N-(4-methylphenyl)amino-2'-carboxybenzophenone, 2-hydroxy-4-N-cyclohexyl amino-2'-carboxybenzophenone, 2-hydroxy-4-N-pyrrolidinyl -2'-carboxybenzophenone, 2-hydroxy-4-N-(2-methylpyrrolidinyl)-2'-carboxybenzophenone, 2-hydroxy-4-N-(3-methylpyrrolidinyl)-2'-carboxybenzophenone, 2-hydroxy-4-N-morpholinyl-2'-carboxybenzophenone, 2-hydroxy-4-N-piperidinyl-2'-carboxybenzophenone, 2-hydroxy-4-N-(2-methylpiperidinyl)-2'-carboxybenzophenone, 2-hydroxy-4-N-(3-methylpiperidinyl)-2'-carboxybenzophenone, 2-hydroxy-4-N-(4-methylpiperidinyl)-2'-carboxybenzophenone, 2-hydroxy-4-N-(4-Dimethylaminophenyl)-2'-carboxybenzophenone, 2-hydroxy-3,5-dimethyl-2'-carboxybenzophenone.

Compounds of formula III are exemplified by, but not limited to; 3-methoxy toluene, 3-methylphenol, 4-methoxy toluene, 4-methylphenol, 2,4-dimethylanisole, 2,4-dimethylphenol, 4-methoxy-2-methyl diphenylamine, 4-hydroxy-2-methyl diphenylamine, 4-methoxy-2,2',4'-trimethyl diphenylamine, 4-hydroxy-2,2',4'-trimethyl diphenylamine, 2-chloro-5-methoxy toluene, 2-chloro-5-hydroxy toluene, 4-methoxy-2-methyl-3'-trifluoromethyl diphenylamine, 4-hydroxy-2-methyl-3'-trifluoromethyl diphenylamine, 4-methoxy-2-methyl-2'-chloro diphenylamine, 4-hydroxy-2-methyl-2'-chloro diphenylamine, 4-methoxy-2-methyl4'-chloro diphenylamine, 4-methoxy-2-methyl-2'-fluoro diphenylamine, 4-hydroxy-2-methyl-2'-fluoro diphenylamine: n-octyl-p-anisidine, N-n-octyl-p-aminophenol, 2-dibenzylamino-5-methoxy-toluene, 4-dibenzylamino-3-methylphenol, 4-methoxy-2-chloro diphenylamine, 4-hydroxy-2-chloro diphenylamine, 4-methoxy-2,3'-dimethyl diphenylamine, hydroxy-2,3'-dimethyl diphenylamine, 4-methoxy-2,4'-dimethyl diphenylamine, 4-hydroxy-2,4'-dimethyl diphenylamine, 3-chloroanisole, 3-chlorophenol, 1-naphthol, 1-methoxy naphthalene, 2-naphthol, 2-methoxy naphthalene, 4-methoxy-2-ethoxyethyl diphenylamine, 4-hydroxy-2-ethoxyethyl diphenylamine, 4-t-butyl phenol, 4-t-butyl anisole, 4-hydroxybenzoic acid, 4-methoxy benzoic acid, 4-hydroxybenzoic acid ethyl ester, 4-methoxy benzoic acid ethyl ester, 3-(p-dimethylamino)anilinoanisole, 3-(p-dimethylamino)anilinophenol, 4-N,N-dibenzylaminophenol, 4-N,N-dibenzylaminoanisidine.

Thus mixtures of fluoran compounds are prepared by reaction between keto acid(s) of formula (II) and compound (s) of formula (III) in the presence of a dehydrating condensation agent, for example, concentrated sulphurc acid, oleum-concentrated sulphuric acid mixtures, polyphosphoric acid, phosphorous pentaoxide or anhydrous aluminium chloride, and mixtures thereof, preferably concentrated sulphuric acid or oleum—concentrated sulphurc acid mixtures, and thereafter bringing the reaction mixture to an alkaline pH in the presence or absence of organic solvent. The solvent, if used, is not specifically limited provided that it is insoluble or only slightly soluble in water. Thus, the solvent may be exemplified by aromatic hydrocarbons such as benzene, toluene, xylenes or trimethyl benzenes, halogenated aromatic hydrocarbons such as chlorobenzene, dichlorobenzenes, chlorobenzenes or bromonaphthalenes, halogenated aliphatic hydrocarbons such as dichloroethane, trichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as amyl alcohol, 2-ethylhexanol or octyl alcohol, ethers such as isopropyl ether, esters such as ethyl acetate or ketones such as cyclohexanone. The solvent may be used singly or as a mixture.

The condensation reaction is generally carried out at from 0 to about 100° C. preferably from about 10 to about 60° C. for several to 100 hours. When the reaction is carried out in concentrated sulphuric acid or oleum-concentrated sulphuric acid mixtures, the reaction temperature is preferably in the range from 0 to about 50° C. The reaction time depends upon the selected reaction temperature and hence the reaction is conducted for a sufficient time to permit the reaction to go to completion. Completion of reaction is determined using standard analytical techniques, including but not limited to, thin layer chromatography, gas chromatography and liquid chromatography.

After the dehydrating condensation reaction is completed the alkali treatment may be carried out by addition of the reaction mass to a stirred mixture of base, water and organic solvent. Suitable bases include, for example, potassium hydroxide, lithium hydroxide, sodium hydroxide, potassium carbonate, sodium carbonate, lithium carbonate, ammonia or organic bases such as triethylamine and mixtures thereof. The preferred bases for use in the process of the present invention are sodium hydroxide and potassium hydroxide. Suitable solvents include toluene, xylene, halogenated aromatic solvents such as chlorobenzene, esters, ethers, ketones, alcohols such as 2-ethylhexanol and mixtures thereof. Additional base may be added as required to achieve an alkalinity within the pH range of 9–12. The treatment may be conducted in a temperature of from 0° C. to the boiling point of the solvent or solvent mixture in use, preferably 50 –100° C. During this process, the mixtures of fluorans according to the present invention can be precipitated from the reaction media. The precipitate may then be isolated by filtration from the reaction liquors.

After isolation, the mixture of fluoran compounds may be washed as desired with water and/or an organic solvent. The solvent may be exemplified by aromatic hydrocarbons such as benzene, toluene, xylenes or trimethyl benzenes, halogenated aromatic hydrocarbons such as chlorobenzene, dichlorobenzenes, trichlorobenzenes or bromonaphthalenes, halogenated aliphatic hydrocarbons such as dichloroethane, trichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as methanol, ethanol, isopropanol, butanol, amyl alcohol, 2-ethylhexanol or octyl alcohol, ethers such as isopropyl ether, or ketones such as cyclohexanone. The solvent may be used singly or as a mixture.

Alternatively, after the dehydrating condensation, the reaction mass may be quenched into a stirred water-solvent mixture at from 0° C. to the boiling point of the water-solvent mixture in use, preferably 50–100° C. The solvent used is not specifically limited provided that it is insoluble or only slightly soluble in water. Thus, the solvent may be exemplified by aromatic hydrocarbons such as benzene, toluene, xylenes or trimethyl benzenes, halogenated aromatic hydrocarbons such as chlorobenzene, dichlorobenzenes, trichlorobenzenes or bromonaphthalenes, halogenated aliphatic hydrocarbons such as dichloroethane, trichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as amyl alcohol, 2-ethylhexanol or octyl alcohol, ethers such as isopropyl ether, or ketones such as cyclohexanone. The solvent may be used singly or as a mixture. Sufficient base, for example potassium hydroxide, lithium hydroxide, sodium hydroxide, potassium carbonate, sodium carbonate, lithium carbonate, ammonia or organic bases such as triethylamine and mixtures thereof, is then added to provide an organic-aqueous phase separation. The aqueous layer may then be separated if desired. To the organic phase or biphasic mixture, containing the phthalide intermediate, is then added further base, as described hereinbefore, to pH>7. The reaction mass is stirred at from 0 to about 100° C., preferably 60–90° C., in order to complete cyclisation to the fluoran product. The reaction mass is then adjusted to 25° C. and the precipitated product may then be isolated by filtration as discussed previously. The reaction product is isolated by filtration from the reaction liquors as the mixture of fluorans of the invention. After isolation, the mixture of fluorans of the invention may be washed with water and/or an organic solvent as defined previously.

The mixture of fluorans of the invention may then be dried by a usual method, such as at a raised temperature, below the melting point of the mixture of fluorans, under vacuum. The composition of the mixture of fluorans so obtained is dependant upon the relative amounts of starting materials used.

A second novel method of preparation is to prepare a mixed keto acid intermediate of general formula (II) from the reaction of aminophenols of general formula (IV) with phthalic anhydrides of general formula (V). Wherein R1, R2 and R5 are as hereinbefore detailed.

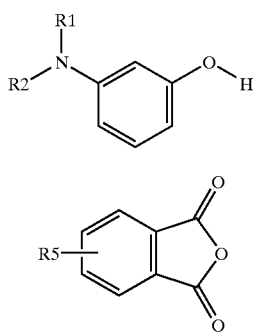

Formula IV

Formula V

A mixture of n different keto acids, where n>1, may be manufactured by the reaction of x different amino phenols of formula (IV) and y different phthalic anhydride derivatives of formula (V) where one or both of x and y are >1.

For instance, a mixed keto acid intermediate consisting of two compounds of general formula (II) may be prepared by reaction of;

i. Two different amino phenols of general formula (IV) with a single phthalic anhydride derivative of formula (V).
ii. Two different phthalic anhydride derivatives of formula (V) with a single amino phenol of general formula (IV).
iii. Recrystallisation of two different keto acid derivatives from a suitable solvent.

Amino phenols of formula IV are exemplified by, but not limited to: N,N-dimethyl aminophenol, N,N-diethyl aminophenol, N,N-di-n-propyl aminophenol, N,N-di-n-butyl aminophenol, N,N-di-n-pentyl aminophenol, N,N-di-n-hexyl aminophenol, N,N-diisopropyl aminophenol, N,N-diisobutyl aminophenol, N,N-diisobutyl aminophenol, N,N-diisoamyl aminophenol, N-methyl-N-cyclohexyl aminophenol, N-methyl-N-phenyl aminophenol, N-methyl-N-(2-methylphenyl)aminophenol, N-methyl-N-(3-methylphenyl)aminophenol, N-methyl-N-(4-methylphenyl) aminophenol, N-methyl-N-propyl aminophenol, N-methyl-N-isopropyl aminophenol, N-methyl-N-butyl aminophenol, N-methyl-N-isobutyl aminophenol, N-methyl-N-secbutyl aminophenol, N-methyl-N-pentyl aminophenol, N-methyl-N-1-methylbutyl aminophenol, N-methyl-N-isoamyl phenol, N-methyl-N-1-methylpentyl aminophenol, N-methyl-N-hexyl aminophenol, N-methyl-N-tetrahydrofurylmethyl aminophenol, N-methyl-N-ethoxypropyl aminophenol, N-methyl-N-cyclohexylmethyl aminophenol, N-methyl-N-phenethyl aminophenol, N-ethyl-N-cyclohexyl aminophenol, N-ethyl-N-phenyl aminophenol, N-ethyl-N-(2-methylphenyl)aminophenol, N-ethyl-N-(3-methylphenyl)aminophenol, N-ethyl-N-(4-methylphenyl)aminophenol, N-ethyl-N-propyl aminophenol, N-ethyl-N-isopropyl aminophenol, N-ethyl-N-butyl aminophenol, N-ethyl-N-isobutyl aminophenol, N-ethyl-N-secbutyl aminophenol, N-ethyl-N-pentyl aminophenol, N-ethyl-N-1-methylbutyl aminophenol, N-ethyl-N-isoamyl phenol, N-ethyl-N-1-methylpentyl aminophenol, N-ethyl-N-hexyl aminophenol, N-ethyl-N-tetrahydrofurylmethyl aminophenol, N-ethyl-N-ethoxypropyl aminophenol, N-ethyl-N-cyclohexylmethyl aminophenol, N-ethyl-N-phenethyl aminophenol, N-propyl-N-cyclohexyl aminophenol, N-propyl-N-phenyl aminophenol, N-propyl-N-(2-methylphenyl)aminophenol, N-propyl-N-(3-methylphenyl)aminophenol, N-propyl-N-(4-methylphenyl)aminophenol, N-propyl-N-isopropyl aminophenol, N-propyl-N-butyl aminophenol, N-propyl-N-isobutyl aminophenol, N-propyl-N-secbutyl aminophenol, N-propyl-N-pentyl aminophenol, N-propyl-N-1-methylbutyl aminophenol, N-propyl-N-isoamyl phenol, N-propyl-N-1-methylpentyl aminophenol, N-propyl-N-hexyl aminophenol, N-propyl-N-tetrahydrofurylmethyl aminophenol, N-propyl-N-ethoxypropyl aminophenol, N-propyl-N-cyclohexylmethyl aminophenol, N-propyl-N-phenethyl aminophenol, N-butyl-N-cyclohexyl aminophenol, N-butyl-N-phenyl aminophenol, N-butyl-N-(2-methylphenyl)aminophenol, N-butyl-N-(3-methylphenyl)aminophenol, N-butyl-N-(4-methylphenyl) aminophenol, N-butyl-N-propyl aminophenol, N-butyl-N-isopropyl aminophenol, N-butyl-N-isobutyl aminophenol, N-butyl-N-secbutyl aminophenol, N-butyl-N-pentyl aminophenol, N-butyl-N-1-methylbutyl aminophenol, N-butyl-N-isoamyl phenol, N-butyl-N-1-methylpentyl aminophenol, N-butyl-N-hexyl aminophenol, N-butyl-N-tetrahydrofurylmethyl aminophenol, N-butyl-N-ethoxypropyl aminophenol, N-butyl-N-cyclohexylmethyl aminophenol, N-butyl-N-phenethyl aminophenol, N-phenyl aminophenol, N-2-methylphenyl aminophenol, N-3-methylphenyl aminophenol, N-4-methylphenyl aminophenol, N-cyclohexyl aminophenol, 3-N-pyrrolidinyl phenol, 3-N-(2-methylpyrrolidinyl)phenol, 3-N-(3-methylpyrrolidinyl)phenol, 3-N-morpholinyl phenol, 3-N-piperidinyl phenol, 3-N-(2-methylpiperidinyl)phenol, 3-N-(3-methylpiperidinyl)phenol, 3-N-(4-methylpiperidinyl) phenol.

Compounds of formula V are exemplified by, but not limited to; phthalic anhydride, terephthalic anhydride, 3-methylphthalic anhydride, 3-nitrophthalic anhydride, 3-hydroxyphthalic anhydride, 3-chlorophthalic anhydride, 3-fluorophthalic anhydride, 4-methylphthalic anhydride, 4-t-butylphthalic anhydride, 4-chlorophthalic anhydride, 4-bromophthalic anhydride, 4-fluorophthalic anhydride, 3,6-dichlorophthalic anhydride, 3,6-dimethylphthalic anhydride, 3,6-difluorophthalic anhydride, 4,5-difluorophthalic anhydride, 4,5-dichlorophthalic anhydride, 1,2-naphthoic anhydride, 2,3-naphthoic anhydride, tetrabromophthalic anhydride, tetrachlorophthalic anhydride, tetraiodophthalic anhydride tetrafluorophthalic anhydride, tetraphenylphthalic anhydride, tetramethylphthalic anhydride, 4-nitrophthalic anhydride, 3-dialkylaminophthalic anhydride, 4-dialkylaminophthalic anhydride.

For the reaction of the mixtures of m-aminophenol derivatives, as above mentioned, with phthalic anhydrides, the latter is usually used in an amount of 0.5–2.0 moles per total moles of the m-aminophenol derivatives. The ratio of solvent to m-aminophenol derivables may be between 0 and 20 parts by weight. The quantity of solvent chosen is dependent on the nature of the m-aminophenol derivatives. The amount of solvent used is determined so that the reaction mass remains mobile throughout the course of the reaction. Preferably, the product is precipitated during the reaction. The reaction is effected at an elevated temperature, preferably in the range of 60–120° C. for a period of 340 hours. The reaction time and temperature are chosen so as to achieve a suitable balance between completion of reaction and the amount of rhodamine type side products that are produced. The amount of rhodamine produced increases at higher temperatures. After the reaction, the reaction mixture is cooled to 0–60° C., most preferably 20–40° C. Dependant on the viscosity of the reaction mixture at this stage, a secondary solvent may be added to the reaction mixture to maintain mobility.

There may be used as the secondary solvent, for example, an aromatic hydrocarbon of 6–10 carbon atoms such as benzene, toluene or xylene, an aliphatic hydrocarbons of 5–12 carbons such as pentane, octane, isooctane, or decane, a halogenated aliphatic, cycloaliphatic or aromatic hydrocarbon of 2–8 carbons, such as perciene, chlorobenzene or dichlorobenzene, ethers such as tetrahydrofuran, dibutyl ether or diphenylether, alcohols such as methanol, ethanol, propanols such as isopropanols or butanols such as n-butanol. There may also be used a mixture of the alcohol with water or a mixture of the alcohol with a hydrocarbon solvent.

The crude keto acid derivative may be recovered from the reaction mixture by filtration, or by diluting the mixture with a solvent in which the derivative is barely soluble and recovering the precipitated derivative by filtration, or by extracting the derivative with an aqueous alkaline solution and precipitating it with acid, or by forming a metal salt of the derivative, isolating the salt and precipitating it with acid.

The organic solvents when used include, for example, an aromatic hydrocarbon of 6–10 carbon atoms such as benzene, toluene or xylene, an aliphatic hydrocarbons of 6–12 carbons such as octane, isooctane, or decane, a halogenated hydrocarbon of 2–8 carbons, aliphatic, cycloaliphatic or aromatic, such as perciene, chlorobenzene or dichlorobenzene, ethers such as tetrahydrofuran, dibutyl ether or diphenylether, among which are especially preferred aromatic hydrocarbons or ethers.

The mixture of keto acids of general formula (II) thus isolated can then be reacted with a compound(s) of general formula (III), as described previously, to produce a mixture of fluorans of formula (I). In this instance the composition of the mixture isolated is determined by the ratio of the amino phenols used.

If desired, the mixture of fluorans, suitably isolated by any of the aforementioned methods, may be further purified by precipitation from an organic solvent or from a organic solvent-water mixture, for example, toluene, benzene, xylene, methanol, ethanol, iso-propanol, n-butanol, acetonitrile, dimethylformamide or mixtures of these solvents. The mixture of fluorans may be dissolved by heating to a temperature range of from room temperature to the boiling point of the chosen solvent, or above it under pressure in an autoclave. After complete dissolution the mixture of fluorans may be precipitated with stirring or on standing.

All of the methods of preparation as hereinbefore described can be used to produce a monophase solid solution of two or more fluoran compounds. Whether or not a monophase solid solution has been formed may be judged by powder X-ray diffraction analysis using K-Cu$\alpha$ rays. A powder X-ray diffraction pattern of a monophase solid solution is substantially identical to that of one of the components, the 'host'. In general the 'host' is the compound forming the greater part of the mixture. A monophase solid solution will also demonstrate a different melting point to that of an equivalent physical mixture. However, a change in melting point may also indicate a mixed crystal has been formed, thus melting point should be considered in conjunction with powder X-ray diffraction when assessing whether or not a monophase solid solution has been formed.

All of the methods of preparation as hereinbefore described can also be used to produce a multiphase solid solution. Whether or not a multiphase solid solution has been formed can be determined by powder X-ray diffraction analysis using K-Cu$\alpha$ rays. A powder X-ray diffraction pattern of a multiphase solid solution will different to a physical mixture of the components in that the signals may be broadened, shifted or altered in intensity. In general, different proportions of the components produce different powder X-ray diffraction patterns.

All of the methods of preparation as hereinbefore described can also be used to produce a mixed crystal. Whether or not a mixed crystal has been formed can be determined by powder X-ray diffraction analysis using K-Cu$\alpha$ rays. A powder X-ray diffraction pattern of a multiphase solid solution will be different to a physical mixture of the components in that the signals may be broadened, shifted or altered in intensity. However, within certain limits, different proportions of the components produce substantially identical powder X-ray diffraction patterns.

The mixtures of fluoran compounds of the general formula (I), as isolated by any of the processes according to the present invention, may be used as a colour forming compound for various recording materials. Isolated material, as defined herein, means both material as obtained from precipitate and filtration as well as material which has been further purified, by, say, recrystallisation.

As such it is a further object of the present invention to provide recording material comprising the mixtures of fluorans of general formula (I) according to the present invention. The recording materials of the present invention include pressure sensitive recording material and heat sensitive recording material.

When used in heat sensitive recording materials, the mixtures of fluorans can be used alone or in combination with other colour forming compounds such as triphenylmethanes, lactones, fluorans, benzoxazines, quinoxalines, phthalides, phenoxazines, phenothiazines, leuco-auramines, rhodamine lactams, spiropyrans and the like in order to adjust the developed hue if desired. The mixtures of fluoran compound of the invention may also be used together with further colour formers to improve the thermal sensitivity and image stability of the recording material. Other colour formers which may be used as above, include but are not limited to; 3-diethylamino-6-methylfluoran, 3-dimethylamino-6-methyl-7-anilinofluoran, 3-diethylamino-6-methyl-7-anilinofluoran, 3-diethylamino-6-methyl-7-(2,4-dimethylanilino)fluoran, 3-diethylamino-6-methyl-7-chlorofluoran, 3-diethylamino-6-methyl-7-(3-trifluoromethylanilino)fluoran, 3-diethylamino-methyl-7-(2-chloroanilino)fluoran, 3-diethylamino-6-methyl-7-(4-chloroanilino)fluoran, 3-diethylamino-6-methyl-7-(2-fluoroanilino)fluoran, 3-diethylamino-6-methyl-7-(4-n-octylanilino)fluoran, 3-diethylamino-7-(4-n-octylanilino)fluoran, 3-diethylamino-7-(n-octylamino)fluoran, 3-diethylamino-7-(dibenzylamino)fluoran, 3-diethylamino-6-methyl-7-(dibenzylamino)fluoran, 3-diethylamino-6-chloro-7-methylfluoran, 3-diethylamino-7-t-butylfluoran, 3-diethylamino-7-carboxyethylfluoran, 3-diethylamino-6-chloro-7-anilinofluoran, 3-diethylamino-6-methyl-7-(3-methylanilino)fluoran, 3-diethylamino-6-methyl-7-(4-methylanilino)fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino)fluoran, 3-diethylamino-7-(2-chloroanilino)fluoran, 3-diethylamino-7-(2-fluoroanilino)fluoran, 3-diethylamino-benzo[a]fluoran, 3-diethylamino-benzo[c]fluoran, 3-dibutylamino-6-methyl fluoran, 3-dibutylamino-6-methyl-7-anilinofluoran, 3-dibutylamino-6-methyl-7-(2,4-dimethylanilino)fluoran, 3-dibutylamino methyl-7-(2-chloroanilino)fluoran, 3-dibutylamino methyl-7-(4-chloroanilino)fluoran, 3-dibutylamino-6-methyl-7-(2-fluoroanilino)fluoran, 3-dibutylamino-4-methyl-7-(3-trifluoromethylanilino)fluoran, 3-dibutylamino-6-ethoxyethyl-7-anilinofluoran, 3-dibutylamino-6-chloro-anilinofluoran, 3-dibutylamino-6-methyl-7-(4-methylanilino)fluoran, 3-dibutylamino-7-(2-chloroanilino)fluoran, 3-dibutylamino-7-(2-fluoroanilino)fluoran, 3-dipentylamino-6-methyl-7-anilinofluoran, 3-dipentylamino-6-methyl-7-(4-2-chloroanilino)fluoran, 3-dipentylamino-7-(3-trifluoromethylanilino)fluoran, 3-dipentylamino-6-chloro-7-anilinofluoran, 3-dipentylamino-7-(4-chloroanilino)fluoran, 3-pyrrolidino-6-methyl-7-anilinofluoran, 3-piperidino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-6-methyl-7-anilinofluoran, 3-cyclohexylamino-6-chlorofluoran, 2-methyl-6-p-(p-dimethylaminophenyl)aminoanilinofluoran, 2-methoxy-6-p-(p-dimethylaminophenyl)aminoanilinofluoran, 2-chloro-3-methyl-6-p-(p-phenylaminophenyl)aminoanilinofluoran, 2-diethylamino-6-p-(p-dimethylaminophenyl) aminoanilinofluoran, 2-phenyl-6-methyl4-p-(p-phenylaminophenyl)aminoanilinofluoran, 2-benzyl-6-p-(p-phenylaminophenyl)aminoanilinofluoran, 3-methyl-6-p-(p-dimethylaminophenyl)aminoanilinofluoran, 3-diethylamino-6-p-(p-diethylaminophenyl) aminoanilinofluoran, 3-diethylamino-6-p-(p-dibutylaminophenyl)aminoanilinofluoran, 2,4-dimethyl-6-[(4dimethylamino)anilino]fluoran, 3-[(4-dimethylaminophenyl)amino]-5,7-dimethylfluoran, 3,6,6'-tris(dimethylamino)spiro[fluorene-9,3'-phthalide], 3,6,6'-tris(diethylamino)spiro[fluorene-9,3'-phthalide], 3,3-bis(p-dimethylaminophenyl)-6-dimethylaminophthalide, 3,3-bis(p-dimethylaminophenyl)phthalide, 3,3-bis-[2-(p-dimethylaminophenyl)-2-(p-methoxyphenyl)ethenyl-4,5,6,7-tetrabromophthalide, 3,3-bis-[2-(p-dimethylaminophenyl)-2-(p-methoxyphenyl)ethenyl-4,5,6,7-tetrachlorophthalide, 3,3-bis[1,1-bis(4-pyrrolidinophenyl)ethylene-2-yl]-4,5,6,7-tetrabromophthalide, 3,3-bis-[1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindole-3-yl)4azaphthalide, 3-(4-diethylamino-2-ethoxyphenyl)-3-(1-octyl-2-methylindole-3-yl)-4-azaphthalide, 3-(4-cyclohexylethylamino-2-methoxyphenyl)-3-(1-ethyl-2-methylindole-3-yl)-4-azaphthalide, 3,3-bis(1-ethyl-2-methylindole-3-yl)phthalide, 3,3-bis(1-octyl-2-methylindole-3-yl)phthalide, mixture of 2-phenyl4-(4-diethylaminophenyl)4-(4-methoxyphenyl)6-methyl-7-dimethylamino-3,1-benzoxazine and 2-phenyl-(4-diethylaminophenyl)-4-(4-methoxyphenyl)-8-methyl-7-dimethylamino-3,1-benzoxazine, 4,4'-[1-methylethylidene)bis(4,1-phenyleneoxy-4,2-quinazolinediyl)]bis[N,N-diethylbenzenamine], bis(N-methyldiphenylamine)-4-yl-(N-butylcarbazole)-3-yl-methane and mixtures thereof.

When preparing a heat sensitive recording material of the invention, the mixture of fluoran compounds of the formula (I) of the present invention and a developer are pulverised separately in water or a suitable dispersing medium, such as aqueous polyvinyl alcohol, to form an aqueous or other dispersion. Optionally, a fine dispersion of sensitiser may be included. The fine particle dispersions thus obtained are combined and then mixed with conventional amounts of binder, filler and lubricant.

Representative examples of the developer which are suitable for use in the heat sensitive recording material include but are not limited to: substituted phenols and bisphenols such as 4,4'-isopropylidene Bisphenol, 4,4'-sec-butylidene bisphenol, 4,4'-cyclohexylidene Bisphenol, 2,2-bis-(4-hydroxyphenyl)-4-methylpentane, 2,2-dimethyl-3,3-di(4-hydroxyphenyl)butane, 2,2'-dihydroxydiphenyl, 1-phenyl-1,1-bis(4-hydroxyphenyl)butane, 4-phenyl-2,2-bis(4-hydroxyphenyl)butane, 1-phenyl-2,2-bis(4-hydroxyphenyl)butane, 2,2-bis(4-hydroxy-3'-methylphenyl)-4-methylpentane, 2,2-bis(4'-hydroxy-3'-tert-butylphenyl)-4-methylpentane, 4,4'-sec-butylidene-bis(2-methylphenol), 4,4'-isopropylidene-bis(2-tert-butylphenol), 2,2-bis(4'-hydroxy-3'-isopropylphenyl)methylpentane, allyl-4,4-bis(4'-hydroxyphenyl)pentanoate, propargyl-4,4-bis(4'-hydroxyphenyl)pentanoate, n-propyl-4,4-bis(4'-hydroxyphenyl)pentanoate, 2,4-bis(phenylsulfonyl)phenol, 2-(4-methylsulfonyl)-4-(phenylsulfonyl)phenol, 2-(phenylsulfonyl)-4-(4-methylsulfonyl)phenol, 2,4-bis(4- methylphenylsulfonyl)phenol, pentamethylene-bis(4-hydroxybenzoate), 2,2-dimethyl-3,3-di(4-hydroxyphenyl)pentane, 2,2-di(4-hydroxyphenyl)hexane; sulphur containing bisphenols such as; 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether; hydroxybenzoate esters such as; benzyl-4-hydroxybenzoate, ethyl-4-hydroxybenzoate, propyl-4-hydroxybenzoate, isopropyl-4-hydroxybenzoate, butyl hydroxybenzoate, isobutyl-4-hydroxybenzoate; hydroxy sulfones such as; 4,4'-dihydroxydiphenyl sulfone, 2,4'-dihydroxydiphenyl sulfone, 4-hydroxy-4'-methyldiphenyl sulfone, 4-hydroxy4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, 4,4'-dihydroxy-3,3',5,5'-tetrabromodiphenyl sulfone; sulphonyl ureas such as 4,4'-bis(p-toluenesulphonylaminocarbonylamino)diphenylmethane; diesters of 4-hydroxyphthalic acid such as; dimethyl 4-hydroxyphthalate, dicyclohexyl 4-hydroxyphthalate, diphenyl 4-hydroxyphthalate; salicylic acid derivatives such as; 4-[2-(4-methoxyphenyloxy)ethyloxy]salicylate, 3,5-di-tert-butylsalicylic acid, 3-benzyl salicylic acid, 3-(α-methylbenzyl)salicylic acid, 3-phenyl-5-(α,α-dimethylbenzyl)salicylic acid, 3,5-di-α-methylbenzyl salicylic acid; metal salts of salicylic acid such as zinc salicylate; benzoic acid derivatives such as; 2-benzylsulfonylbenzoic acid, 3-cyclohexyl hydroxybenzoic acid; metal salts of benzoic acid such as; zinc benzoate, zinc 4-nitrobenzoate; resorcylic anilide derivatives as described in U.S. Pat. No. 5,607,894 and included herein by reference; phthalic acid and isophthalic acid derivatives such as; 4-(4'-phenoxybutoxy)phthalic acid, 4-(2'-phenoxyethoxy)phthalic acid, 4-(3'-phenylpropyloxy)phthalic acid, mono(2-hydroxyethyl)-5-nitro-isophthalic acid, 5-benzyloxycarbonyl isophthalic acid, 5-(1'-phenylethanesulfonyl) isophthalic acid and bis(1,2-dihydro-1,5-dimethyl-2-phenyl-3H-pyrrol-3-one-O)bis(thiocyanato-N)zinc and mixtures thereof.

Representative binders used for the heat sensitive recording material includes, but are not limited to; polyvinyl alcohol (fully and partially hydrolysed), carboxy, amide, sulfonic and butyral modified polyvinyl alcohols, derivatives of cellulose such as hydroxyethyl cellulose, methyl cellulose, ethyl cellulose, carboxymethyl cellulose and acetyl cellulose, copolymer of styrene-maleic anhydride, copolymer of styrene-butadiene, polyvinyl chloride, polyvinyl acetate, polyacrylamide, polyamide resin and mixtures thereof.

Exemplary fillers which can be used include, but are not limited to; calcium carbonate, kaolin, calcined kaolin, aluminium hydroxide, talc, titanium dioxide, zinc oxide, silica, polystyrene resin, urea-formaldehyde resin, hollow plastic pigment and mixtures thereof.

Representative lubricants for use in heat sensitive recording materials include, but are not limited to; dispersions or emulsions of stearamide, methylene bisstearamide, polyethylene, camauba wax, paraffin wax, zinc stearate or calcium stearate and mixtures thereof.

Other additives can also be employed, if necessary. Exemplary additives include sensitisers, stabilisers and the like.

Representative sensitisers for use in heat sensitive recording materials include but are not limited to; stearamide, methylol stearamide, p-benzylbiphenyl m-terphenyl, 2-benzyloxynaphthalene, dibenzyl oxalate, di(4-methylbenzyl)oxalate, di(4-chlorobenzyl)oxalate, dimethyl phthalate, dibenzyl terephthalate, dibenzyl isophthalate, 1,2-diphenoxyethane, 1,2-bis(4-methylphenoxy)ethane, 1,2-bis(3-methylphenoxy)ethane, 4,4'-dimethylbiphenyl, phenyl-1-hydroxy-2-naphthoate, 4-methylphenyl biphenyl ether, 1,2-bis(3,4-dimethylphenyl)ethane, 2,3,5,6-4'-methyldiphenyl methane, 1,4-diethoxynaphthalene, o-xylylene-bis(phenyl ether), 4-(m-methylphenoxymethyl)biphenyl, p-hydroxyacetanilide, p-hydroxybutylanilide, p-hydroxynonananilide, p-hydroxylauranilide, p-hydroxyoctadecananilide and mixtures thereof.

Representative stabilisers for use in heat sensitive recording materials include but are not limited by; 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane, bis(3-tert-butyl-4-hydroxy-6-methylphenyl)sulfone, bis(3,5-dibromo-4-hydroxyphenyl) sulfone, 4,4'-sulfinyl bis(2-tert-butyl-5-methylphenol), 2,2'-methylene bis(4,6-di-tert-butylphenyl)phosphate and alkali metal, ammonium and polyvalent metal salts thereof, 4-benzyloxy-4'-(2-methylglycidyloxy)diphenyl sulfone, 4,4'-diglycidyloxydiphenyl sulfone, 1,4-diglycidyloxybenzene, 4-[α-(hydroxymethyl)benzyloxy]-4-hydroxydiphenyl sulfone, metal salts of p-nitrobenzoic acid, metal salts of phthalic acid mono benzyl ester, metal salts of cinnamic acid and mixtures thereof.

The coating liquid obtained by the addition of additives to the particle dispersion of fluoran and developer can be applied to a suitable substrate such as paper, plastic sheet and resin coated paper, and used as the heat sensitive recording material. The system of the invention can be employed for other end use applications using colour forming materials, for example, a temperature indicating material.

The mixtures of fluorans of the present invention may also be used in conventional pressure sensitive recording materials as described in GB 2,000,206 and GB 2,068,994. They may be used alone or in combination with other colour forming materials such as those listed previously herein. In pressure sensitive recording materials, a solution of colour formers is allowed to come into contact with an acidic developer to produce the image. Typical solvents used include but are not limited to; diisopropyl naphthalene, butylated biphenyls, isopropylated biphenyls, phenyl xylyl ethane, butylated diphenylethane, xylenyl xylene, esters of trimethylol propane, biodegradable solvents of natural or synthetic origin such as rapeseed oil, sunflower oil, coconut oil, palm oil, dialkyl esters of carboxylic acids such as adipic acid, sebacic acid and azaleic acid. The solvent may be diluted with diluents exemplified by, but not limited to; kerosenes, normal paraffins and naphthenic oils. Typical developers include but are not limited to; activated bentonite, activated montmorillonite, synthetic aluminosilicates, phenolic resins especially Zinc modified phenolic resins, attapulgite clay, Silton clay and zinc salicylates.

Preferably, the colour former solution is encapsulated in microcapsules thus preventing contact with the developer and premature image development. Typical microcapsule wall materials include but are not limited to; gelatine, melamine-formaldehyde(MF), urea-formaldehyde(UF), MF-UF, polyurea, polyurethane and polyamide. Typically, the microcapsules containing the colour former may be coated on to a sheet of paper (coated back or CB) and the developer may be coated onto a separate sheet of paper (coated front or CF). The imaging set may then be formed by bringing together the two coated papers with the coated surfaces in contact with each other. Pressure may then be applied to the reverse of the CB to rupture the microcapsules and allow the colour former solution to come into contact with the developer on the CF and form the desired image. If more than one copy is required, one or more intermediate sheets. Usually known as CFB (coated front and back) sheets are provided, each of which is coated on it's lower surface with microcapsules and on it's upper surface with colour developer composition. The microcapsules and colour developing material may also be coated onto the same surface of a sheet usually known as a self-contained system.

The following non-limiting examples illustrate the processes of the present invention;

EXAMPLE 1

Preparation of Monophase Solid Solution From Reaction of 2'-Carboxy-4-diethylamino-2-hydroxybenzophenone (10 mol %) and 2'-Carboxy-4-dibutylamino-2-hydroxybenzophenone (90 mol %) With 4-Methoxy-2-methyidiphenylamine To 249.5 g of 98% sulphuric acid and 61.2 g oleum was added. 78.97 g of 2'-carboxy-4-dibutylamino-2-hydroxybenzophenone and 7.44 g of 2'-carboxy-4-diethylamino-2-hydroxybenzophenone over about 2 hr with the temperature being maintained below about 25° C. by use of an ice-bath. Once in solution, 50.7 g of 4-methoxy-2-methyldiphenylamine was added and the mixture was stirred for about 3 hr at 30° C. The reaction mass was then added, over about 30 minutes with stirring, to a mixture of 135 g toluene-45 g water at 85° C. To this was then added, over 30 minutes, 135.7 g water. Agitation was ceased and the separated aqueous phase was removed. To the remaining organic phase was added 244 g sodium hydroxide 100° TW, 199 g toluene and 387 g water and the reaction was stirred for 2 h at 85° C. The reaction was cooled to 25° C. and the precipitated product was isolated by filtration. The product was washed with hot water (about 60° C.) then methanol and dried to yield 106.2 g of a monophase solid solution of the invention (melting point 179.9–181.4° C.). The composition of the monophase solid solution was confirmed by dissolving the crystalline compound in toluene to release the component fluorans. Standard analytical techniques, such as thin layer chromatography, high pressure liquid chromatography and gas chromatography can be used to confirm the ratio of the two components in the monophase solid solution.

EXAMPLE 2

Preparation of a Mixture of Fluoran Compounds From Reaction of 2'-Carboxy-4-diethylamino-2-hydroxybenzophenone (54 mol %) and 2'-Carboxy-4-dibutylamino-2-hydroxybenzophenone (46 mol %) With 4-Methoxy-2-methyldiphenylamine To 232.3 g of 98% sulphuric acid and 83.6 g oleum was added, 44 g of 2'-carboxy-4-dibutylamino-2-hydroxybenzophenone and 449 of 2'-carboxy-4-diethylamino-2-hydroxybenzophenone over about 2 hr with the temperature being maintained below about 25° C. by use of an ice-bath. Once in solution, 59.7 g of 4-methoxy-2-methyidiphenylamine was added and the mixture was stirred for about 2 hr at 30° C. The reaction mass was then added, over about 30 minutes with stirring, to a mixture of 137 g toluene-36 g water at 85° C. To this was then added, over 30 minutes, 202.6 g water and 91.4 g sodium hydroxide 100° TW. Agitation was ceased and the separated aqueous phase was removed. To the remaining organic phase was added methanol 12.4 g, 245.6 g sodium hydroxide 100° TW, 205.8 g toluene and 362.4 g water and the reaction was stirred for 2 h at 85° C. The reaction was cooled to 25° C. and the aqueous layer was removed. Solvent was then removed by steam distillation and the precipitated product was isolated by filtration. The composition of the mixture of fluorans was confirmed by chromatography.

EXAMPLE 3

Preparation of a Mixture of Fluorans From Phthalic Anhydride (52 mol %) and 3-Methylphthalic Anhydride (48 mol %)

An amount of 72 g (0.44 mol) of N,N-diethylaminophenol, 35.4 g (0.24 mol) phthalic anhydride, 35.4 g (0.22 mol) 3-Methylphthalic anhydride and 98.3 g of toluene were placed in a reactor, and stirred whilst the reaction mass was heated to 90° C. over 2 hours and then heated to 107° C. and stirred at this temperature for 6 hours.

Toluene 167 g was added and the reaction mass cooled to 20° C. overnight. The product was isolated by filtration. The crude product was washed with methanol to yield 73.2 g of the mixed keto acid.

The mixed keto acid was then converted to the mixed fluoran using the method described in example 1.

EXAMPLE 4

Preparation of a Mixture of Fluorans From 3-N-(1-Ethylpropyl)-N-propylaminophenol (90 mol %) and 3-N,N-Diethylaminophenol (10 mol %)

An amount of 3.3 g (0.02 mol) of N,N-diethylaminophenol, 39.8 g (0.18 mol) 3-N-(1-ethylpropyl)-N-propylaminophenol, 32.6 g (0.22 mol) phthalic anhydride and 46 g of toluene were placed in a reactor, and stirred whilst the reaction mass was heated to 90° C. over 2 hours and then heated to 85° C. and stirred at this temperature for 12 hours. Toluene 40 g was added and the reaction mass cooled to 20° C. The product was isolated by filtration. The crude product was washed with methanol to yield 41.6 g of the mixed keto acid. The mixed keto acid was then converted to the mixed fluoran as described in example 1.

EXAMPLE 5

Preparation of a Mixture of Fluoran Compounds From Reaction of 2'-Carboxy-4-dibutylamino-2-hydroxybenzophenone With 4-Methoxy-2-methyidiphenylamine (90 mol %) and 4-Methoxy-2,3'-dimethyldiphenylamine (10 mol %)

The mixture of fluorans was prepared as in example 1 but with 2'-carboxy-4-dibutylamino-2-hydroxybenzophenone (100 mol %) being used in place of the mixture of 2'-carboxy-4-dibutylamino-2-hydroxybenzophenone (90 mol %) and 2'-carboxy diethylamino-2-hydroxybenzophenone (10 mol %) and a mixture of 4-methoxy-2-methyidiphenylamine (90 mol %) and 4-methoxy-2,3'-dimethyldiphenylamine (10 mol %) being used in place of 4-methoxy-2-methyldiphenylamine (100 mol %). The resulting product was a white solid with melting point (179.3–180.7° C.).

EXAMPLE 6

Preparation of a Mixture of Fluoran Compounds From Reaction of 2'-Carboxy-4-dibutylamino-2-hydroxybenzophenone With 4-Methoxy-2-methyidiphenylamine (90 mol %) and Dibenzyl-p-anisidine (10 mol %)

The mixture of fluorans was prepared as in example 1 but with 2'-carboxy-4-dibutylamino-2-hydroxybenzophenone (100 mol %) being used in place of the mixture of 2'-carboxy-4-dibutylamino-2-hydroxybenzophenone (90 mol %) and 2'-carboxy-4-diethylamino-2-hydroxybenzophenone (10 mol %) and 4-methoxy-2-methyldiphenylamine (90 mol %) and dibenzyl-p-anisidine (10 mol %) being used in place of of 4-methoxy-2-methyldiphenylamine (100 mol %). The resulting product was a white solid with melting point (181–183° C).

A heat sensitive recording material including a monophase solid solution prepared according to the present invention was prepared as follows:

EXAMPLE 7

Preparation of Heat Sensitive Coating Formulations Comprising the Monophase Solid Solution Prepared According to the Invention Dispersions A–C were prepared by grinding the compositions shown below in an attritor until an average particle size of $1\mu$ was attained.

| Dispersion A (Colour Former) | |
| --- | --- |
| Monophase solid solution of Example 1 | 3.01 parts |
| Polyvinyl alcohol (10% aq. soln.) | 10.50 parts |
| Water | 6.49 parts |
| Dispersion B (Colour Developer) | |
| Bis Phenol A | 7.5 parts |
| Polyvinyl alcohol (10% aq. soln.) | 7.5 parts |
| Water | 22.5 parts |
| Dispersion C (Sensitiser) | |
| p-Benzylbiphenyl | 10.0 parts |
| Polyvinyl alcohol (10% aq. soln.) | 10.0 parts |
| Water | 20.0 parts |

A thermal coating mixture was then prepared by combining together the following components

| | parts by weight |
| --- | --- |
| Dispersion A | 6.6 |
| Dispersion B | 10.0 |
| Dispersion C | 6.0 |
| Calcium Carbonate (25% aq. dispersion) | 12.0 |
| Zinc stearate (33% aq. dispersion) | 0.9 |
| Polyvinyl alcohol (10% aq. soln) | 4.5 |
| Tinopal ® ABP-X (fluorescent whitening agent) | 0.12 |
| Water | 2.48 |

This coating mixture was applied on one side of a base paper weighing 50 g/m2 in a coating weight of about 5.0 g/m2, and then dried. The resulting sheet was calendered by means of a laboratory calender to produce a recording sheet with excellent background whiteness.

The heat sensitive recording paper obtained by a process of the invention demonstrates excellent background whiteness (brightness) of paper after application of the coating liquid and in storage stability, i.e. resistance to light, heat and moisture, of uncoloured portion of the coated paper and good resistance of the image to water and plasticiser. Additionally, the recording paper obtained shows a high dynamic sensitivity.

Evaluation of water resistance was conducted by immersing a facsimile image in de-ionised water for 24 hours at room temperature and then observing the remaining image density. Evaluation of plasticiser resistance was made by contacting a facsimile image with a sheet of PVC under 100 gcm$^{-2}$ pressure for 5 hours at 50° C. and observing the remaining image density.

Evaluation of sensitivity was done using an Infotec fax machine 3301 at pulse widths of 0.30. 0.50. 0.68 and 1.00 milliseconds.

Evaluation post application was conducted by observing the brightness of the paper. Evaluation of light resistance was conducted by inspecting the degree of yellowing of the uncoloured portion of the paper after exposure to 120 hours of artificial daylight. Evaluation of heat and moisture resistance was conducted by examining the soiling of the uncoloured portion of paper after storage at 60° C. and 50% relative humidity for one hour

EXAMPLE 8

Evaluation of the Use of Mixtures of Fluorans of the Invention in Pressure Sensitive Recording Material 2% solutions of the mixtures of fluorans of the present invention were prepared in diisopropylnaphthalene/kerosene (70:30 w/w). These solutions were then gravure printed on to commercially available clay, phenolic resin and zinc salicylate CF papers. After one hour, the L*, a* and b* values were measured using a Gretag SPM 50 spectrophotometer.

| Example | CF | L* | a* | b* |
| --- | --- | --- | --- | --- |
| Monophase solid solution of example 1 | Clay | 58.6 | 6.05 | −5.03 |
| Monophase solid solution of example 1 | Zinc salicylate | 63.56 | 6.22 | 3.82 |
| Monophase solid solution of example 1 | Phenolic Resin | 62.30 | 5.99 | 1.06 |
| Mixture of fluorans of example 2 | Clay | 59.77 | 7.20 | −4.71 |
| Mixture of fluorans of example 2 | Zinc Salicylate | 63.89 | 6.60 | 3.58 |
| Mixture of fluorans of example 2 | Phenolic Resin | 61.91 | 6.07 | 0.59 |
| Mixture of fluorans of example 5 | Clay | 59.95 | 5.47 | −4.98 |
| Mixture of fluorans of example 5 | Zinc Salicylate | 64.17 | 5.34 | 3.61 |
| Mixture of fluorans of example 5 | Phenolic Resin | 62.77 | 5.56 | 1.10 |
| Mixture of fluorans of example 6 | Clay | 58 | −2.31 | −3.51 |
| Mixture of fluorans of example 6 | Zinc Salicylate | 64 | −1.22 | 3.43 |
| Mixture of fluorans of example 6 | Phenolic Resin | 64 | −1.83 | 1.80 |

The L*, a*, b* values obtained demonstrate the ability of the mixtures of fluoran compounds of the invention to be used in pressure sensitive copying systems.

What is claimed is:

1. A process for the manufacture of mixtures of fluoran compounds by the reaction of keto acids of formula (II) with a compound of formula (III) in the presence of a dehydrating condensation agent:

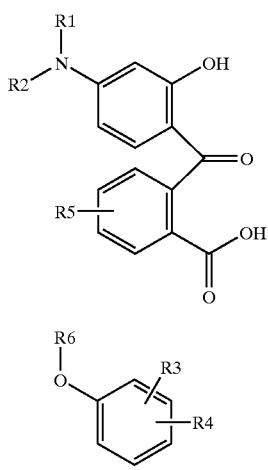

Formula II

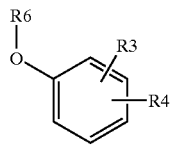

Formula III wherein,
- R1 and R2 independently represent hydrogen, an alkyl of 1–18 carbon, a secondary alkyl with respect to the carbon atom bonded to the nitrogen atom of 3–13 carbon atoms, a cycloalkyl of 4–8 carbon atoms or a phenyl, both of which may be substituted by at least one substituent selected from the group consisting of halogen atoms and alkyls having 1–4 carbon atoms, an aralkyl of 7–10 carbon atoms; or R1 and R2, together with the adjacent nitrogen atom form a heterocyclic ring;
- R3 is hydrogen, an alkyl of 1–4 carbon atoms, an alkoxy of 1–4 carbon atoms, a phenyl; a substituted phenyl or a halogen;
- R4 is an alkyl group of 1–18 carbon atoms, a carboxyalkyl of 1–18 carbon atoms, a carboxycycloalkyl of 4–8 carbon atoms, an alkylamino of 1–18 carbon atoms, a cycloalkylamino of 4–8 carbon atoms, a dialkylamino or dicycloalkylamino; an arylamino, a substituted arylamino; an aralkylamino of 7–10 carbon atoms; a diaralkylamino;
- R5 is an alkyl of 1–18 carbon atoms, a carboxy alkyl of 1–18 carbon atoms or a halogen and
- R6 is hydrogen or alkyl of 1–4 carbon atoms.

2. A process according to claim 1 wherein the dehydrating condensation agent is selected from: concentrated sulphuric acid, oleum—concentrated sulphuric acid mixtures, polyphosphoric acid, phosphorous pentaoxide or anhydrous aluminium chloride, and mixtures thereof.

3. A process according to claim 2 wherein the dehydrating condensation agent is selected from: concentrated sulphuric acid or oleum-concentrated sulphuric acid mixtures.

4. A process according to claim 1 wherein the condensation reaction is carried out at from 0 to about 100° C.

5. A process according to claim 4 wherein the condensation reaction is carried out at from about 10° C. to about 60° C.

6. A process according to claim 1 wherein the reaction mixture comprising keto acids of formula (II) and compound of formula (III) is brought to an alkaline pH after the addition of the dehydrating condensation agent.

7. A process according to claim 1 wherein the reaction mixture comprising keto acids of formula (II) and compound of formula (III) is quenched into a stirred water-solvent mixture after the addition of the dehydrating condensation agent.

8. A process according to claim 1 for the manufacture of mixtures of fluoran compounds comprising two fluoran components designated A and B.

9. A process according to claim 1 for the manufacture of mixtures of fluoran compounds comprising two components designated A and B wherein the ratio of the components A to B is in the range of from 0.1–99%.

10. A process according to claim 1 wherein the fluoran mixture comprises two components designated A and B in the stated ratios:
- 3-dibutylamino-6-methyl-7-anilinofluoran (95%), 3-dibutylamino-7-dibenzylaminofluoran (5%);
- 3-dibutylamino-6-methyl-7-anilinofluoran (90%), 3-diethylamino-6-methyl-7-anilinofluoran (10%);
- 3-dibutylamino-6-methyl-7-anilinofluoran (46%), 3-diethylamino-6-methyl-7-anilinofluoran (56%);
- 3-diethylamino-6-methyl-7-anilinofluoran (52%), 3-diethylamino-6,3'(4')-dimethyl-7-anilinofluoran (48%);
- 3-diethylamino-6-methyl-7-anilinofluoran (10%), 3-N-(1-ethylpropyl)-N-propylamino-6-methyl-7-anilinofluoran (90%); and
- 3-dibutylamino-6-methyl-7-m-tolylaminofluoran (10%), 3-dibutylamino-6-methyl-7-anilinofluoran (90%).

11. A heat sensitive recording material comprising a mixture of fluorans according to claim 1 in combination with a developer, a dispersing medium and optionally another colour forming material, a binder, a sensitiser, a filler, a lubricant or a stabiliser and mixtures thereof.

12. A pressure sensitive recording material comprising a mixture of fluorans according to claim 1 in combination with other known colour forming materials, a solvent, a developer and optionally a diluent and a capsule wall material.

13. A mixture of fluoran compounds obtainable by the reaction of mixed keto-acids of formula (II), derived from the reaction of compounds of formula (IV) with compounds of formula (V), together with the compounds of formula (III):

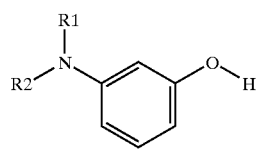

Formula IV

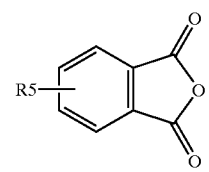

Formula V wherein
- R1 and R2 independently represent hydrogen; an alkyl of 1–18 carbon, a secondary alkyl with respect to the carbon atom bonded to the nitrogen atom of 3–13 carbon atoms; a cycloalkyl of 4–8 carbon atoms or a phenyl, both of which may be substituted by at least one substituent selected from the group consisting of halogen atoms and alkyls having 1–4 carbon atoms, an aralkyl of 7–10 carbon atoms; or R1 and R2 together with the adjacent nitrogen atom form a heterocyclic ring;

R3 is hydrogen; an alkyl of 1–4 carbon atoms; an alkoxy of 1–4 carbon atoms; a phenyl; a substituted phenyl or a halogen;

R4 is an alkyl group of 1–18 carbon atoms; a carboxyalkyl of 1–18 carbon atoms; a carboxycycloalkyl of 4–8 carbon atoms; an alkylamino of 1–18 carbon atoms; a cycloalkylamino of 4–8 carbon atoms; a dialkylamino or dicycloalkylamino, an arylamino; a substituted arylamino; an aralkylamino of 7–10 carbon atoms; a diaralkylamino;

R5 is an alkyl of 1–18 carbon atoms; a carboxy alkyl of 1–18 carbon atoms or a halogen.

* * * * *